United States Patent [19]

Lepain et al.

[11] 4,430,888

[45] Feb. 14, 1984

[54] SYSTEM FOR THE RAPID ANALYSIS OF WATER-BORNE OIL SPILLS

[75] Inventors: Andre Lepain, Rosiere; Robert Bronchart, Brussels; Roger Remacle, Lasne, all of Belgium

[73] Assignee: Labofina, S.A., Belgium

[21] Appl. No.: 440,937

[22] Filed: Nov. 12, 1982

Related U.S. Application Data

[62] Division of Ser. No. 230,637, Feb. 2, 1981, Pat. No. 4,388,407.

[51] Int. Cl.³ ............................................. G01N 9/04
[52] U.S. Cl. .................................. 73/61.1 R; 422/99
[58] Field of Search .................... 73/53, 61 R, 61.1 R, 73/61.4; 422/99, 102

[56] References Cited

U.S. PATENT DOCUMENTS

| | | | |
|---|---|---|---|
| 1,052,391 | 2/1913 | Valerius et al. | 73/61 R X |
| 2,379,158 | 6/1945 | Kalischer | 73/61.4 X |
| 3,485,086 | 12/1969 | Roman | 73/61 R |
| 3,540,292 | 11/1970 | Darbo | 422/99 X |

Primary Examiner—Gerald Goldberg
Assistant Examiner—Joseph W. Roskos
Attorney, Agent, or Firm—Michael J. Caddell

[57] ABSTRACT

A system is disclosed for rapid on-site analysis of a water-borne oil-slick, which system utilizes a combination of devices designed to permit on-site determination of the water content and specific gravity of the oil/water mixture, and the initial boiling point of the water-free oil.

1 Claim, 5 Drawing Figures

SYSTEM FOR THE RAPID ANALYSIS OF WATER-BORNE OIL SPILLS

This application is a division of Ser. No. 230,637, filed Feb. 2, 1981, now U.S. Pat. No. 3,388,407.

The present invention relates to a simple process and to an apparatus for the rapid determination of the characteristics of an oil-pollutant on the very site where it is spilled on water surfaces, beaches and coasts.

It is well known that, when crude petroleum or petroleum fractions is poured on a water surface, and particularly on sea water, the oil remains on the surface and then forms a continuous slick which tends to spill. These oil slicks are naturally undesirable because they prevent the transfer of oxygen and light, which are necessary to the marine life.

On the other hand, if these oil slicks are not dispersed within a short period of time, these oil slicks age or blow with sea water to form an emulsion, usually called "chocolate mousse" which is practically undispersible, providing thereafter ecological problems.

The breadth of these ecological problems mainly depends on the rapidity with which one intervenes with suitable means. These latter should necessarily be adapted to the pollutant to eliminate. However, the working of the suitable means to eliminate the pollutant may be realized only after the determination of some characteristics of the pollutant which is to be treated However, these determinations are generally not carried out on the very site, but in laboratories, that provides losses of time due to the transport of the samples to be tested between the site and those laboratories.

Therefore, it is essential and even imperious to possess much more rapidly the necessary information in order to work the suitable means as soon as possible to efficacely eliminate the pollutant.

As it is very difficult, for longitical reasons, to transfer on the site the material of a laboratory together with sophisticated products, there is therefore a need for a simple material, extremely usual products and methods which are necessary not derivated from specialized and advanced laboratory procedures, to determine the main characteristics of the pollutant to be eliminated.

The Applicant has now found a process and an apparatus which enable to reach the object of the invention.

An object of the present invention is to provide a process and an apparatus for the rapid determination of the characteristics of an oil-pollutant, using simple material and methods and usual products.

Another object of the present invention is to provide a process and an apparatus for the rapid determination of the characteristics of an oil-pollutant which are directly applicable on the site.

The process and the apparatus of the present invention for the rapid determination of the characteristics of a water containing oil-pollutant consist in:

(a) determining the water content of the mixture water-pollutant
- by introducing into the upper part of a glass tube, separated from the lower part by a tap, a cup filled with the mixture water-pollutant, a sufficient amount of solvent for oil products, practically water insoluble, having a specific gravity significantly higher than that of water and a water repellent coalescent agent,
- by closing the upper aperture of said tube by means of a plug,
- by stirring said tube up to complete solubilization of the water-pollutant mixture into said solvent,
- by opening the tap separating the upper part of the tube from the lower part to enable decantation of the mixture into two phases, the aqueous phase coming above the organic phase,
- by placing the graduation zero of a plate previously standardized in percent of water and mobile along the lower part of the tube, in front of the upper meniscus of the aqueous phase, the graduation of the mobile plate in front of the lower meniscus of the aqueous phase, giving the water content of the water-pollutant mixture;

(b) determining the specific gravity of the water-pollutant mixture
- by hanging at a calibrated spring, introduced into a glass tube which may be hooked at any accessible place, a vessel of known volume, filled with the water-pollutant mixture and closed with a cap which is crossed with the attachment rod of the calibrated spring,
- by reading the graduation indicated on a fixed plate, attached to the glass tube, previously standardized in specific gravity and placed in front of the adjusting mark of the calibrated spring;

(c) determining the initial boiling point of the pollutant
- by introducing into a glass tube, having a closing means at its upper part and a tap at its lower part, a sufficient amount of water-pollutant mixture and a sufficient amount of a water soluble solvent of the glycol type and practically insoluble in the pollutant, favorizing the separation of water out of the mixture water-pollutant,
- by letting the mixture decant up to the formation of two phases the aqueous phase being below the organic phase,
- by eliminating the aqueous phase by opening the tap,
- by thereafter introducing into said glass tube a sufficient amount of a mixture comprising anhydrous calcium chloride and anhydrous sodium sulfate, to perfect the elimination of water present in the organic phase,
- by recovering the sample of pollutant free of water, by opening the tap, calcium chloride and sodium sulfate being kept in the bottom of the glass tube by means of a fritted glass,
- by introducing the sample of water-free pollutant into an apparatus formed by a glass tube comprising a first inclined lateral tube containing a thermometer, and a second lateral tube which is diametrically opposed to the first one and constituted of two horizontal branches linked together by means of a vertical branch, said vertical branch being topped by a vent pipe, said second tube ensuring the reflux of the distilled matter in the glass tube through the different branches, the lower horizontal branch being extended inside the glass tube to favorize the formation of a liquid plug avoiding the exhaust of the vapors directly through the second lateral tube,
- by hooking said device on a metallic cylinder set around the burner of a welding torch supplied with a small gas-bottle,
- by heating the glass tube up to the time where the reflux occurs,
- by noting the temperature indicated on the thermometer at the time where the reflux occurs.

The present invention is also concerned with an apparatus for the determination of the hereabove described characteristics, said apparatus comprising:

a device for the rapid determination of the water content of the mixture water-pollutant, constituted of a narrow and elongated cup of known volume, a vertically placed glass tube constituted to two tubes juxtaposed end to end and linked together by means of an external flange, the upper tube having a constant diameter higher than that of the cup, the lower tube having a constant diameter smaller than that of the upper tube and having a tap at its upper part and a sphere at its lower part, and finally a mobile plate, previously standardized in percent of water, sliding along the lower glass tube;

a device for the rapid determination of the specific gravity of the mixture water-pollutant, constituted of a vertically placed rigid metallic wire, curved at its upper part to form a hook, its lower part being introduced into a glass tube, a calibrated spring hooked at the lower extremity of said metallic wire, said calibrated spring having an adjusting mark at its lower extremity, and a second rigid metallic wire hooked at the lower extremity of the calibrated spring, the lower extremity of the second metallic wire coming out of the bottom of the glass tube, a vessel, filled with the mixture water-pollutant and hooked at the lower extremity of the second rigid metallic wire, and a fixed device, graduated in specific gravity externally linked to the glass tube and placed so that the graduation zero of the device is in front of the adjusting mark of the calibrated spring when the hooked vessel is empty;

a device for the rapid determination of the initial boiling point of the pollutant, constituted of a heating device, comprising a welding torch supplied by a gas-bottle, the horizontal pipe of the welding torch being vertically bent upwards to constitute the head of the burner, said head of burner being placed in a cylindrical metallic enclosure, a vertically placed glass tube containing the pollutant to be tested which is free from water, said glass tube comprising at its upper part a first external lateral tube, inclined upwards wherein a thermometer is introduced so that the bulb of the thermometer reaches the axial part of the glass tube, and a second external lateral tube ensuring condensation and reflux of the distilled products, said second lateral tube being diametrically opposed to the first one, and constituted of two horizontal branches linked together with a vertical branch which is topped with a vent pipe, the extremity of the upper horizontal branch being in front of the thermometer bulb, the lower horizontal branch having, inside the glass tube, a downwards vertical extension of progressively restricted diameter, said glass tube being introduced into the cylindrical metallic enclosure and fixed on it so that the bottom of the glass tube is always at the same height with regard to the flame of the burner, and so that the graduated part of the thermometer is out of the cylindrical metallic enclosure.

The determination of the various characteristics hereabove described in accordance with the process of the invention and by means of the apparatus of the invention enables to rapidly select with certitude the means to be worked for the elimination of the oil-pollutant.

For example, the determination of the water content of the mixture water-pollutant enables to select the most suitable type of recovering device. The determination of the specific gravity allows to foresee the most suitable modalities of trawling to ensure a high yield of recovering.

The determination of the initial boiling point of the pollutant allows to know the temperature range comprising the flash point of the pollutant, by means of a diagram giving the range of flash point versus the initial boiling point. The knowledge of this characteristic is very important for the security of the means to be worked due to the explosion risks.

Other characteristics may also be rapidly determined by means of methods using a simplified material. In this field, it may be cited, the determination of the viscosity by means of a bead-drops viscosimeter or a flow gage if the liquid is very viscous, or still the determination of pour point or the freezing point, or still the determination of the reaction of the pollutant with regard to some usual dispersants and deemulsifiers.

The present invention is now described by reference to the drawings wherein.

Figure 1:
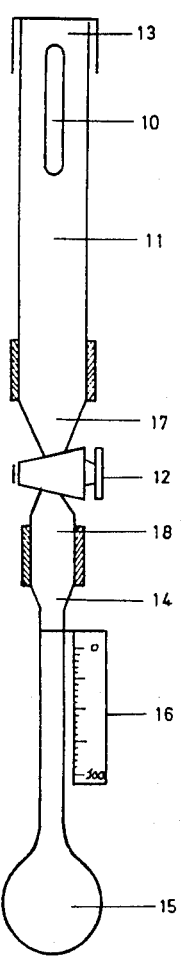
FIG. 1 is a diagram of the device for the determination of the water content of the mixture water-pollutant.

By means of the device described on FIG. 1, the water content of the mixture water-pollutant is determined by first filling the cup (10) to the brim with the mixture water-pollutant. The cup may have any form possible inasmuch it may be easily introduced into the glass tube (11) and may freely move into said tube (11).

The cup (10), filled with the mixture water-pollutant, is first introduced into tube (11), tap (12) being closed. Thereafter, a solvent for oil products, pratically water insoluble and whose specific gravity is higher then that of water, containing a water repellent coalescent agent is introduced into tube (11). Said solvent has to be a usual solvent and generally chloroform or carbone tetrachloride is used. Tube (11) is thereafter closed by means of a plug (13) and the device is stirred up to complete dissolution of the mixture water-pollutant. At this time, tap (12) is opened and the liquid is let to flow into tube (14) which is terminated by a sphere (15). The liquid breaks up into two phases, one organic phase and one aqueous phase, the aqueous phase being above the organic phase due to the specific gravity of the solvent. The graduation zero of the mobile plate (16) sliding along the tube (14) is slid in front of the upper meniscus of the aqueous phase, the graduation being in front of the lower meniscus of the aqueous phase gives the percentage of water. The mobile plate (16) has been previously graduated in water percents. The scale of the graduations depends on the volume of the cup (10) and on the diameter of tube (14) along which the mobile plate 16 slides.

According to a preferred embodiment of the device of the present invention, the cup (10) is narrow and elongated in order to be easily introduced into tube (11). The device is preferably constituted of three detachable pieces comprising the tube (11), a central piece comprising tap (12) topped with tube (17) linked to tube (11) by means of an external flange on the one hand, and extended with a tube (18) linked to tube (14) by means of an external flange on the other hand. Preferably, tube (14) has a smaller diameter than that of tube (11) in order to improve the precision of the reading.

Figure 2:
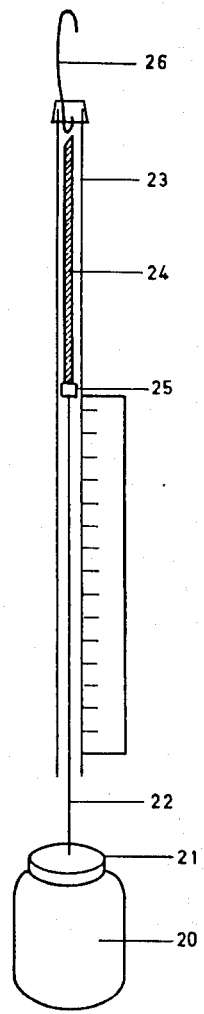
FIG. 2 is a diagram of the device for the determination of the specific gravity of the mixture water-pollutant.

By means of the device described on FIG. 2, the specific gravity of the mixture water-pollutant is determined by first filling a vessel (20) closed by means of a cap (21) wherein a rigid metallic yarn (22) is hooked. The upper part of said metallic yarn (22) is introduced into a glass tube (23) and the upper extremity of said metallic yarn (22) is hooked at the lower extremity of a calibrated spring (24). The lower extremity of the calibrated spring (24) has an adjusting mark (25) which is in front of the graduation zero of a fixed plate, when nothing is hung at the metallic yarn (22), said fixed plate has previously been standardized in specific gravity and is externally hooked on the glass tube (23). The upper extremity of the calibrated spring (24) which is always inside the glass tube (23), is hooked on the lower extremity of a rigid metallic yarn (26) whose the upper part comes out of the glass tube (23) and is curved in the form of a hook.

The length of the course of the calibrated spring (24), in the glass tube (23) has been settled to obtain a good precision of the measure. Generally the length of the course is about 10 cm for a range of specific gravity comprised between 0.6 and 1.

Figures 3, 4:
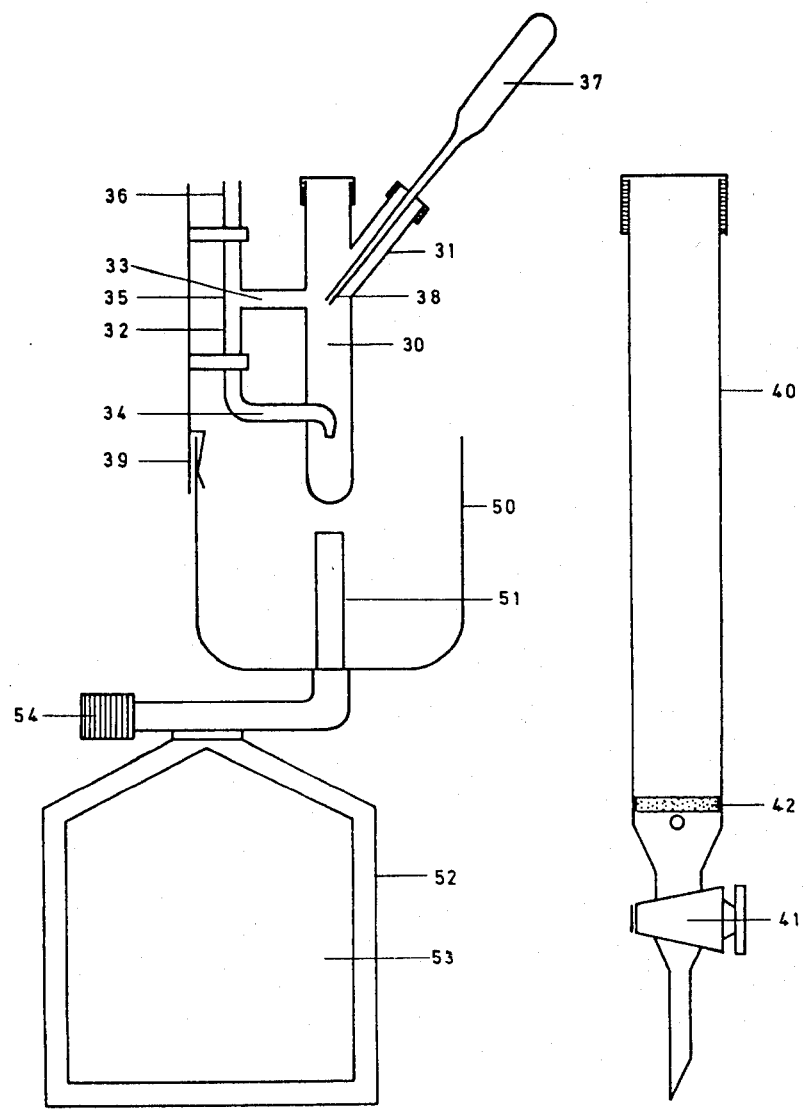
FIG. 3 is a diagram of the device for the determination of the initial boiling point of the pollutant.
FIG. 4 is a diagram of the device for removing water from the mixture water-pollutant.

By means of the device described on FIG. 3, the initial boiling point of the water-free pollutant is determined. The removal of water from the mixture water-pollutant is carried out by means of the device described on FIG. 4. This removal is carried out by introducing a sufficient amount of the mixture water-pollutant together with water-soluble solvent, which is practically insoluble in the oil-pollutant, into a glass tube (40) extended at its lower extremity by a tap (41) and having in its lower part a fritted glass (42). The used solvent is generally of the glycol type and more particularly propyleneglycol. These types of solvent are not cumbersome for the determination of the initial boiling point of the pollutant because their boiling point is substantially higher than that of light components that the oil pollutant may contain. The tube (40) is then closed, while tap (41) is also closed and the device is stirred to extract water from the oil-pollutant. The mixture breaks up into two phases, one aqueous phase containing water and the solvent, the other phase containing the pollutant. Tap (41) is then opened and the aqueous phase is let to flow. In order to remove the last traces of water present in the oil-pollutant, a sufficient amount of a mixture comprising anhydrous calcium chloride and anhydrous sodium sulfate is introduced into tube (40). The mixture is stirred and thereafter the liquid phase is recovered. Said liquid phase consists of the water-free pollutant, while the mixture of calcium chloride and sodium sulfate is kept on the fritted glass (42). The recovered amount of pollutant is then treated in the device described on FIG. 3.

The amount of water-free pollutant is introduced into a vertical glass tube (30) comprising an externally inclined upwards lateral tube (31) and a second lateral tube (32) diametrically opposed to the first one. The lateral tube (32) has two horizontal branches (33) and (34) linked together by a vertical branch (35) topped with a vent pipe (36). The branch (34) extends inside the tube (30), said extension being vertically placed downwards, and having a diameter which is progressively restricted in order to act as a liquid plug during the distillation of the products. Said tube (32) is foreseen to ensure the condensation and the reflux of the distilled products through tube (30). A thermometer (37) is introduced in tube (31) and the bulk (38) of the former is placed in the axial part of tube (30) and in front of branch (33) of tube (32).

Said device is hooked on a vertically placed cylindrical metallic enclosure (50), by means of a fastening clips.

The pollutant is distilled by heating with the burner (51) of a welding torch (52) supplied by a small gas-bottle (53). The horizontal pipe (54) linking the gas-bottle (53) to the head of the burner (51) is vertically curved upwards in order to place the head of the burner into the metallic enclosure (50).

When the pollutant in tube (30) is heated, the vapors rise in tube (30), condense on the thermometer (37) and in branch (33) which is eventually cooled by means of a piece of wet cotton-whool; the condensate flowing through branches (35) and (34) ensures the reflux to tube (30) and forms the liquid plug, so that the vapors cannot directly rise through branches 34, 35 and 36. When the reflux is established and when drops drip on the bulb (38) of thermometer (37), the distillation is in steady state and then temperature may be read on the thermometer (37). This value of temperature is transferred on a diagram giving the range of flash point of the pollutant versus its initial boiling point.

The following example is given in order to better illustrate the present invention but without limiting its scope.

EXAMPLE

The following experiment was carried out with a pollutant containing 22% of crude petroleum and 78% of water. Said pollutant was present as a reverse emulsion of the chocolate mousse type. The specific gravity of the mixture water-pollutant was 1.01 and the flash point of the pollutant was 36° C. These last characteristics were determined with precision.

The process and the apparatus of the invention were then used to determine the different characteristics of the pollutant.

First the cup was filled to the brim with the mixture water-pollutant. Said cup was introduced into the glass tube described on FIG. 1. Thereafter, 100 ml chloroform together with 2 drops of primary oleic amine acetate as water repellent coalescent agent were introduced in this glass tube. The mixture was let to flow into the lower tube through the tap, and the water content of the mixture water-pollutant was determined in accordance with the hereabove described method. It was found that the water content was 72%.

The vessel described on FIG. 2 was then filled with the mixture water-pollutant to determine its specific gravity.

The vessel filled to the brim was hung to the device described on FIG. 2 and the specific gravity found was 1.03.

Thereafter, 40 ml of the mixture water-pollutant were introduced into the glass tube described on FIG. 4, together with 60 ml of propylene-glycol.

After decantation of the mixture into 2 phases, the aqueous phase was eliminated. In the same tube, 20 g of a 4/1 mixture of $CaCl_2$ and $Na_2SO_4$ were introduced. The mixture was stirred and the water-free pollutant was recovered.

The recovered amount of water-free pollutant was introduced into the glass tube described on FIG. 3, the burner of the welding torch was lighted in order to distillate the pollutant. When the reflux was established, a drop dipped on the bulb of the thermometer. The temperature indicated by the thermometer was 105° C.

Figure 5:
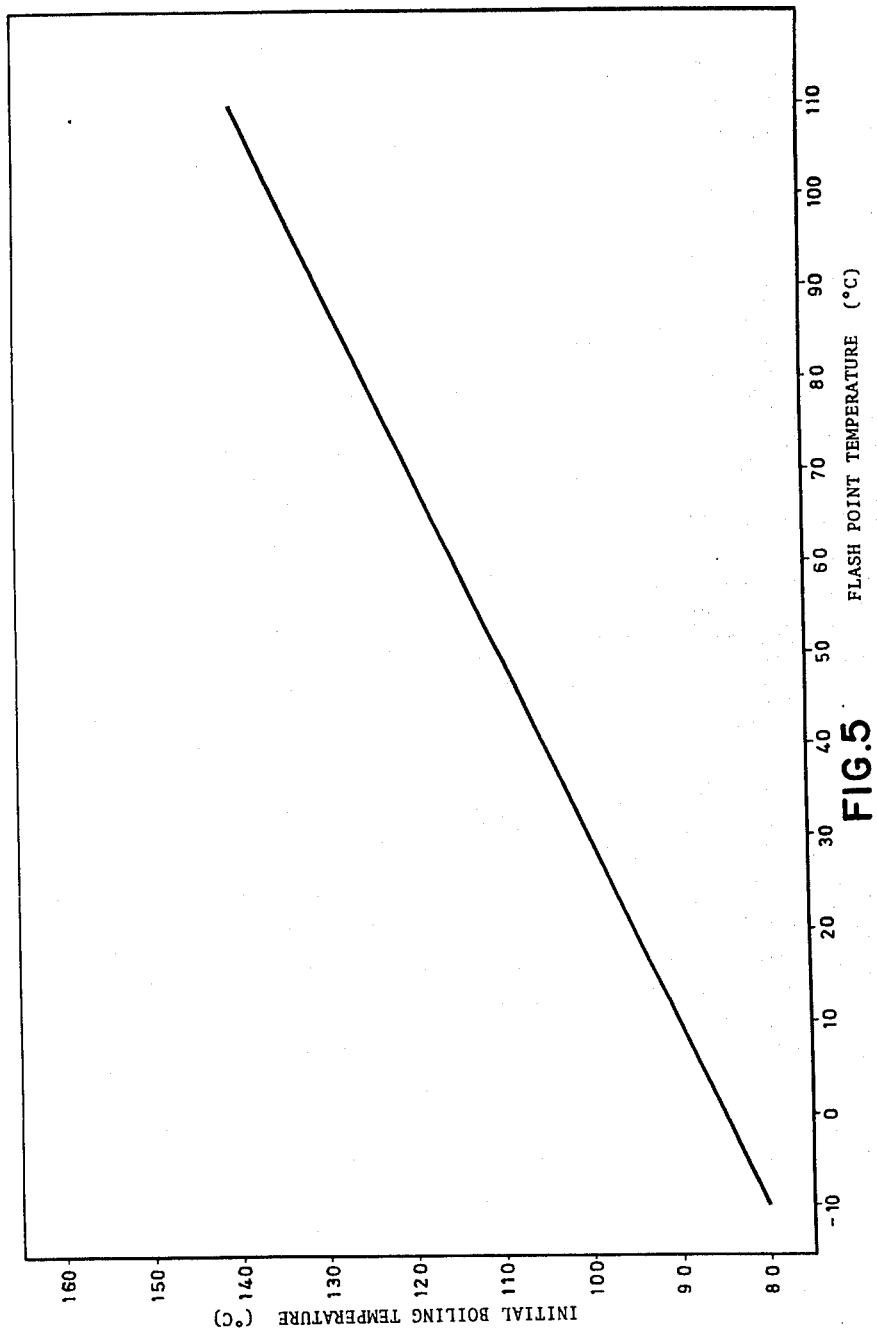
FIG. 5 is a diagram giving the range of flash point versus the initial boiling point of the pollutant.

This temperature was transferred on the diagram of FIG. 5, and the flash point corresponding to this temperature was 39° C.

It will be noticed that the determination of the characteristics of the pollutant in accordance with the process of the invention is of sufficient precision to select the means to work for eliminating the oil-pollutant.

What we claim is:

1. Apparatus for the rapid determination of the water content of a water-containing oil pollutant comprising a narrow elongated cup (10) of known volume, a pair of vertically disposed glass tubes (11, 14) juxtaposed end to end and linked together by flow control means, the upper tube (11) having a constant diameter larger than that of cup 10 which is self-contained within tube (11), the lower tube (14) having a constant diameter smaller than that of the upper tube (11) and having said flow control means comprising a tap (12) at its upper part, an enlarged lower end (15), and a movable plate 16, previously standardized in percent of water slidably located vertically along the lower glass tube (14).

* * * * *